US010610614B2

(12) United States Patent
Hotokebuchi et al.

(10) Patent No.: US 10,610,614 B2
(45) Date of Patent: *Apr. 7, 2020

(54) BIOIMPLANT WITH EVANESCENT COATING FILM

(71) Applicants: KYOCERA CORPORATION, Kyoto (JP); Takao Hotokebuchi, Kyoto (JP)

(72) Inventors: Takao Hotokebuchi, Fukuoka (JP); Iwao Noda, Osaka (JP)

(73) Assignee: KYOCERA CORPORATION, Kyoto (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/017,309

(22) Filed: Jun. 25, 2018

(65) Prior Publication Data

US 2018/0361022 A1 Dec. 20, 2018

Related U.S. Application Data

(63) Continuation-in-part of application No. 12/440,430, filed as application No. PCT/JP2007/066119 on Aug. 20, 2007, now Pat. No. 10,004,604.

(30) Foreign Application Priority Data

Sep. 8, 2006 (JP) .................................. 2006-244479
Sep. 19, 2006 (JP) .................................. 2006-252933

(51) Int. Cl.
| A61L 27/32 | (2006.01) |
| A61L 27/54 | (2006.01) |
| A61L 27/42 | (2006.01) |
| A61L 27/06 | (2006.01) |
| A61L 27/30 | (2006.01) |

(52) U.S. Cl.
CPC .............. *A61L 27/32* (2013.01); *A61L 27/06* (2013.01); *A61L 27/306* (2013.01); *A61L 27/425* (2013.01); *A61L 27/54* (2013.01); *A61L 2300/104* (2013.01); *A61L 2300/404* (2013.01); *A61L 2300/606* (2013.01); *A61L 2420/02* (2013.01); *A61L 2420/04* (2013.01); *A61L 2430/24* (2013.01)

(58) Field of Classification Search
CPC ................ A61L 27/32; A61L 2420/02; A61L 2300/404; A61L 2300/606; A61L 27/54; A61L 2300/112; A61L 2420/04; A61L 2430/24; A61L 27/06; A61L 27/306; A61L 27/425; A61L 2300/104; A61F 2310/00598

See application file for complete search history.

(56) References Cited

U.S. PATENT DOCUMENTS

| 5,732,469 A | 3/1998 | Hamamoto et al. |
| 6,113,993 A | 9/2000 | Gao et al. |
| 6,207,218 B1 | 3/2001 | Layrolle et al. |
| 6,365,028 B1 | 4/2002 | Shatrov |
| 6,582,715 B1* | 6/2003 | Barry ...................... A61L 27/02 424/422 |
| 6,994,883 B2 | 2/2006 | Layrolle et al. |
| 8,821,911 B2 | 9/2014 | Gan |
| 2001/0024662 A1* | 9/2001 | Yang ...................... A61L 24/02 424/489 |
| 2001/0036530 A1* | 11/2001 | Noda .................. A61F 2/30767 428/104 |
| 2005/0221259 A1* | 10/2005 | Anderson ............ A61C 8/0012 433/201.1 |
| 2006/0210494 A1 | 9/2006 | Rabiei et al. |
| 2009/0198344 A1 | 8/2009 | Prentice |
| 2009/0215009 A1 | 8/2009 | Noishiki et al. |
| 2017/0119932 A1 | 5/2017 | Mawatari |

FOREIGN PATENT DOCUMENTS

| CA | 2416201 A1 | 1/2003 |
| CN | 1454101 A | 11/2003 |
| EP | 0410711 A1 | 1/1991 |
| EP | 1231299 B1 | 1/2012 |
| JP | 4-144555 A | 5/1992 |
| JP | 2001-518827 A | 10/2001 |
| JP | 2004-503333 A | 2/2004 |
| JP | 2005-506879 A | 3/2005 |
| JP | 2005-097052 A | 4/2005 |
| JP | 2005-523380 A | 8/2005 |
| JP | 2005-297435 A | 10/2005 |
| JP | 2006-151729 A | 6/2006 |
| KR | 20060056093 A * | 5/2006 |

(Continued)

OTHER PUBLICATIONS

KR-20060056093-A, Espacenet English translation, downloaded in Jun. 2019 (Year: 2019).*

Iwao Noda et al., "Ginkei Kokin Seitai Zaiiyo no Kaihatsu (1)—Gin HA Yosha Gijutsu no Kaihatsu to Gin Ion Yoshutsu Tokusei", Japanese Society for Study of Bone and Joint Infections Program Shorokushu, vol. 30, p. 43, 2007.

Chinese Office Action for Application No. 200780033447.7 dated Jan. 11, 2012.

Faust et al., "Biofunctionalised Biocompatible Titania Coatings for Implants", Key Emerging Materials, vols. 206-213, 2002, p. 1547-1550.

Giavaresi et al., "Histomorphometric, ultrastructural and microhardness eveluation of the osseointegration of nanostructured titanium oxide coating by metal-organic chemical vapour deposition: an in vivo study", Biomaterials, vol. 25, 2004, p. 5583-5591.

(Continued)

Primary Examiner — Mark V Stevens
(74) Attorney, Agent, or Firm — Duane Morris LLP (57) ABSTRACT

To provide a bioimplant capable of controlling a rate of an antibacterial agent and an antibiotic to be eluted from the coating film. An evanescent coating film made of a calcium phosphate-based material having crystallinity of 90% or less is formed at a predetermined area of the bioimplant and an antibacterial agent or an antibiotic is contained in the coating film. If necessary, a metal oxide layer made of a metal oxide having an isoelectric point of less than 7 is formed on the bioimplant thereby suppressing adhesion of bacteria.

20 Claims, 6 Drawing Sheets

(56) References Cited

FOREIGN PATENT DOCUMENTS

| WO | 98/42390 A1 | 10/1998 |
|---|---|---|
| WO | 9931303 A1 | 6/1999 |
| WO | 0112883 A1 | 2/2001 |
| WO | 02/05862 A1 | 1/2002 |
| WO | 03/035123 A1 | 5/2003 |
| WO | 03/055449 A1 | 7/2003 |
| WO | 2005/027801 A1 | 3/2005 |
| WO | 2006/033956 A2 | 3/2006 |
| WO | 2006/104628 A2 | 10/2006 |
| WO | 2007/022211 A1 | 2/2007 |
| WO | 2007/089894 A2 | 8/2007 |
| WO | 2009053670 A2 | 4/2009 |

OTHER PUBLICATIONS

Japanese Office Action dated Apr. 17, 2012, for Application No. 2006-244479 with the English translation.
Japanese Office Action dated May 15, 2012, for Application No. 2006-252933 with the English translation.
Lee et al., "Hydroxyapatite-TiO2 Hybrid Coating on Ti Implants", Journal of Biomaterials Applications, vol. 20, Jan. 2006, p. 195-208.
Lin et al., "Characterization of Electrolytic TiO2 Coating on Ti for Biomedical Applications", Journal of the Electrochemical Society, vol. 151, No. 12, 2004, p. D127-D133.
Macionczyk et al., "Repassivationg tantalum/tantalum oxide surface modification on stainless steel implants", Surface and Coatings Technology, vols. 142-144, 2001, p. 1084-1087.
Müller et al., "Surface engineering of Stainless steel materials by covalent collagen immobilization to improve implant biocompatibility", Biomaterials, vol. 26, 2005, p. 6962-6972.
Yao et al., "Anodization: A Promising Nano-Modification Technique of Titanium Implants for Orthopedic Applications", Journal of Nanoscience and Nanotechnology, vol. 6, 2006, 2682-2692.
Yen et al., "Characterization of electrolytic ZrO2 coating on Co—Cr—Mo implant alloys of hip prosthesis", Biomaterials, vol. 22, 2001, p. 125-133.
Ando et al. (In Vitro Antibacterial Properties of Thermal Sprayed Silver-Containing Hydroxyapatite Coating against Methicillin-Resistant *Staphylococcus aureus*, Poster No. 1125, 54th Annual Meeting of the Orthopaedic Research Society, 1 page. Meeting date Mar. 2-5, 2008).
Documentation of meeting date for Ando reference, [Retrieved from internet <URL: http://www.ors.org/past-meetings/>], [Downloaded Sep. 30, 2016], 1 page.
Kofstad et al., Oxidation of titanium in the temperature range of 800-1200° C., Journal of the Less Common Metals, Apr. 1961, vol. 3, Issue 2, pp. 89-97, [Retrieved from internet <URL: http://www.sciencedirect.com/science/article/pii/0022508861900017>],Abstract only (2 pages).
Kofstad et al., High-temperature oxidation of titanium, Journal of the Less Common Metals, Jun. 1967, vol. 12, Issue 6, pp. 449-464, [Retrieved from internet <URL: http://www.sciencedirect.com/science/article/pii/0022508867900173 >], Abstract only (2 pages).
Murakami et al. (Evaluation of the structure of Ag in thermal sprayed Ag-containing hydroxyapatite coatings, Journal of the Chemical Society of Japan (2015), 123 (8): 667-671).
Chen et al. (In vitro anti-bacterial and biological properties of magnetron co-sputtered silver-containing hydroxyapatite coating, Biomaterials (on-line Jul. 26, 2006) 27:5512-5517) (6 pages).
Noda et al. (Development of Novel Thermal Sprayed Antibacterial Coating and Evaluation of Release Properties of Silver Ions, Journal of Biomedical Materials Research Part B: Applied Biomaterials (avail. on-line Oct. 20, 2008), pp. 456-465) (10 pages).
Yang et al. (A review on calcium phosphate coatings produced using sputtering process—an alternative to plasma spraying, Biomaterials (2005) 26: 327-337 (cited by Chen, as ref. 39)) (11 pages).
Xue et al. (Effect of hydroxyapatite coating crystallinity on dissolution and osteointegration in vivo, Journal of Biomedical Materials Research Part A (Wiley Interscience, published online Jul. 15, 2005), vol. 74 A, Issue 4, pp. 553-561 ) (9 pages).
Xue bibliographic information for verification of Journal information, [Retrieved from Internet <URL: http://onlinelibrary.wiley.com/doi/10.1002/jbm.a.30323/abstract >], (printed Mar. 5, 2016), 3 pages.
Lee et al, (In vitro characterization of postheat-treated plasma-sprayed hydroxyapatite coatings, Surface Coatings & Technology (2005; available on-line Nov. 11, 2004) 197: 367-374), 8 pages.
JP 1994-069582 (machine translation for U.S. Appl. No. 11/816,811, which was published as Noishiki et at., US 2009/0215009 A1) (cited on IOS filed Nov. 23, 2011), 4 pages.
Mukherjee et al. (Antimicrobial activity of aluminium oxide nanoparticles for potential clinical applications (Science against microbial pathogens: communicating current research and technological advances, A. Mendez-Vilas, Ed. (Formatex, 2011), pp. 245-251 [From internet <URL: http://www.formatex.info/microbiology3/book/245-251.pdf ), 7 pages.
Clyne et al. (2.1 Fundamental Studies of the PEO Process (pub. Univ. Cambridge, UK; Composites and Coatings Group, Dept. of Materials Science and Metallurgy) [From internet <URL: http://www.ccg.msm.cam.ac.uk/directory/research-themes/plasma-electrolytic-oxide-coatings/2.1-fundamental-studies-of-the-peo-process>] Clyne et al. [Downloaded Feb. 19, 2014], 3 pages.
Keronite PEO (Keronite, What is plasma electrolytic oxidation? [Retrieved from internet <URL: http://www.keronite.com/page-view.php?pagename=What-is-Plasma-Electrolytic-Oxidation? >] [Downloaded Feb. 19, 2014], 1 page).
Keronite Properties (Keronite, General Properties of Keronite Layers, [Retrieved from internet <URL: http://www.keronite.com/page-view.php?pagename=Plasma-Electrolytic-Oxidation-Material-Characteristic s >] [Downloaded Feb. 19, 2014], 1 page).
Overgaard et al. (The influence of crystallinity of the hydroxyapatite coating on the fixation of implants: Mechanical and Histomorphometric Result, The Journal of Bone and Joint Surgery, (British Editorial Society of Bone and Joint Surgery, 1999), vol. 81-B, No. 4., pp. 725-731), 7 pages.
Dumbleton et al. (Hydroxyapatite-Coated Prostheses in Total Hip and Knee Arthoplasty, Journal of Joint and Bone Surgery (British) (Nov. 2004) 86 (11): 2526-2540; available from ProQuest), 16 pages.

\* cited by examiner

Joint cartilage

Normal hip joint

Artificial hip joint

BIOIMPLANT WITH EVANESCENT COATING FILM

CROSS REFERENCE TO RELATED APPLICATIONS

This is a continuation-in-part of U.S. application Ser. No. 12/440,430 entitled "Bioimplant for Artificial Joint With Evanescent Coating Film," filed on Mar. 6, 2009 as a U.S. National Phase Application of PCT International Application No. PCT/JP2007/066119, filed Aug. 20, 2007, which claims priority to Japanese Application Nos. JP2006-244479 and JP2006-252933, filed on Sep. 8, 2006 and Sep. 19, 2006, respectively. Each of the above prior applications are incorporated by reference herein in their entireties.

FIELD OF THE INVENTION

The present invention relates to a bioimplant comprising an evanescent coating film containing an antibacterial agent or an antibiotic.

BACKGROUND OF THE INVENTION

With the increase of active population and aging population, the use of a bioimplant for the treatment of both osteo-injury and bone disease has continued to expand. The use of a bone substitute for bone crush and bone removal or the use of supports for embrittled bone require that an artificial bone substitute forms a strong joint or ossifies with the natural bone and therefore ensures structural integrity. When an adjacent structure is porous and is equivalent to bone, the bone grows into the adjacent structure. However, it is considered necessary not only for the bone to grow into the porous structure, but also that there should exist bonding which enables strong adhesion between the natural bone growing into the porous structure and the bioimplant. The bioimplant requires a high strength since it is used in a state of being fixed in the bone, and a stainless steel, a cobalt-chromium alloy and a titanium alloy are mainly used. Ceramics having excellent in vivo corrosion resistance and sliding characteristics, such as alumina and zirconia, and plastics such as ultrahigh molecular weight polyethylene are also used.

An important requirement for fixation of a bioimplant to bone is that the bone grows on and/or into the surface of the bioimplant. Various studies disclose that a calcium phosphate coating on an implant made of cobalt-chromium (Co—Cr) or a titanium (Ti) alloy, for example, a biologic apatite accelerates bone adhesion more quickly than if the implant made of the alloy has a non-coated surface. The biologic apatite $Ca_{10}(PO_4)_6(OH)_2$ is one of the main compounds which constitute human bone and teeth. The synthesized hydroxyapatite (HA) closely resembles a natural apatite and thus has been used in a study in which HA is used in dental and orthopedic implants. An implant has been produced which is easily integrated with neighboring bones and tissues by coating with HA or other crystalline calcium phosphates after transplantation.

However, when bacteria are propagated in an artificial joint after an operation of the joint and cause infectious diseases, the infected artificial joint is withdrawn by an operation and the infection is treated with an antibiotic (for several weeks to several months), and then the replacement of the artificial joint is performed. When the prognosis is poor, irremediable problems such as immobilization of a joint and amputation of hands and feet occur. Therefore, there are proposed a method of coating a hydroxyapatite film having high crystallinity and large specific surface area, which is suited for impregnation with an antibiotic, by precipitating hydroxyapatite on the surface of an implant and drying the hydroxyapatite, and a therapeutic agent-impregnated implant in which the coating film is impregnated with the antibiotic (Published Japanese Translation No. 2005-506879 of the PCT Application).

SUMMARY OF THE INVENTION

The crystalline hydroxyapatite is suited for impregnation with the antibiotic. However, since the coating film has uniform pore size and porosity, it is difficult to perform sustained release of a medicine at a desired rate and thus the medicine tends to be eluted at a fixed rate at a time. When the antibiotic is eluted in this way, there arises a problem that validity cannot be controlled as a result of elimination of antibacterial activity. A water-soluble natural organic antibacterial agent is supported by a structure of a coating film of a crystalline hydroxyapatite and can exert antibacterial activity due to elution from the structure. However, since antibacterial activity is usually lower than that of an inorganic antibacterial agent and resistant bacteria are easily generated in response to the antibiotic, the use of the inorganic antibacterial agent is desired so as to prevent infectious diseases of a bioimplant. However, there is a problem that it is difficult to utilize a phenomenon of elution from a crystalline hydroxyapatite film since the inorganic antibacterial agent is insoluble.

The present inventors have found that when crystallinity of the coating film of the crystalline hydroxyapatite is adjusted to 90% or less, evanescence of the coating film in vivo is attained and thus not only the evanescence rate can be controlled by the crystallinity and composition, but also the evanescence period can be adjusted by the thickness of the film.

The present invention has been completed based on such a finding and the gist lies in a bioimplant comprising an implant and an evanescent coating film made of a calcium phosphate-based material having crystallinity of 90% or less formed at a predetermined area of the implant, the evanescent coating film containing an antibacterial agent or an antibiotic.

According to the present invention, since an evanescent coating film is formed at a predetermined area of an implant and an antibacterial agent or antibiotic is contained in the coating film, the release rate of the antibacterial agent can be controlled by the evanescence rate of the film. The evanescence rate of the film depends on the crystallinity of the film and the composition of the film, while the evanescence period of the film depends on the evanescence rate and the thickness of the film. Therefore, adjustment of these conditions enables the creation of an optimum antibacterial environment in a predetermined area for a predetermined period. Moreover, since the antibacterial agent is released utilizing evanescence of the film, it becomes possible to use an insoluble inorganic antibacterial. Accordingly, an effective aspect capable of preventing postoperative infectious diseases can be constituted depending on a requirement, and it is possible to avoid worst-case situations such as withdrawal and replacement of an artificial joint, immobilization of a joint upon bad prognosis, and amputation of hands and feet.

DETAILED DESCRIPTION OF THE PREFERRED EMBODIMENTS

The gist of the present invention lies in a bioimplant comprising an implant and an evanescent coating film made of a calcium phosphate-based material having crystallinity of 90% or less formed at a predetermined area of the implant, the evanescent coating film containing an antibacterial agent or an antibiotic.

The calcium phosphate-based material used in the present invention is composed of one kind or a mixture of two or more kinds which are selected from calcium phosphate-based ceramics containing hydroxyapatite (HA), tri-calcium phosphate (TCP) and tetra-calcium phosphate (TeCP), calcium phosphate-based glass, and calcium phosphate-based glass ceramics.

The composition of the calcium phosphate-based material is one of the factors which control an evanescence rate of the coating film of the present invention, and the evanescence rate can be adjusted by mixing a crystalline hydroxyapatite (HA) as an insoluble calcium phosphate; tri-calcium phosphate (TCP), tetra-calcium phosphate (TeCP) and calcium phosphate-based glass as soluble calcium phosphates; and calcium phosphate-based glass ceramics in an appropriate ratio.

If it is assumed that the evanescence rate of hydroxyapatite in a body fluid is 1, the evanescence rate of .alpha.-TCP is about 10 and that of .beta.-TCP is about 3. It can be understood that the evanescence rate can be adjusted by adjusting the composition of the calcium phosphate-based material. Each evanescence rate obtained by assuming the evanescence rate of hydroxyapatite in a body fluid as 1 is as follows.

TABLE 1

| | Evanescence rate (vs. HA = 1) |
|---|---|
| α-TCP | 10 |
| β-TCP | 3 |
| Tetra-calcium phosphate (TECP) | 2 |
| Calcium phosphate-based glass | 9 |
| Calcium phosphate-based glass ceramics | 5 |

As the film forming method, for example, a thermal spraying method such as flame spraying, high velocity oxygen fuel spraying, or plasma spraying method or a sputtering method; a physical vapor deposition method such as ion plating, ion beam deposition, or ion mixing method; or a wet coating method such as sol-gel method is selected. The film forming method is associated with crystallinity of the formed film. Namely, when the calcium phosphate-based material is coated by the above thermal spraying method or physical vapor deposition method, an amorphous film is usually formed. A crystal film made of HA can be formed by subjecting the amorphous film to a thermal treatment such as vacuum heat treatment, laser heat treatment, or hydrothermal treatment. Although the calcium phosphate-based amorphous film is in a state of being eluted most easily in a body fluid, the elution rate can be controlled more widely than that in the case of crystalline ceramics by adjusting crystallinity using a heat treatment.

For example, sputtering is suited for use in a method for forming a thin film, and an evanescent coating film having crystallinity of 90% or less and a thickness of 0.1 μm or more and less than 5 μm can be formed by sputtering HA having crystallinity of 100%. Such a film has performances which are effective as a short-period evanescent coating film which evanesces within one month.

In contrast, a thermal spraying method is suited for formation of a thick coating film having a thickness of 5 μm or more and less than 100 μm, and a coating film having crystallinity of about 10% is usually formed by thermal spraying of HA having crystallinity of 100%. In this case, it is possible to form a coating film which evanesces after 6 months in a thickness of 20 μm, or evanesces after one month in a thickness of 40 μm. Crystallinity can be increased by subjecting to a heat treatment and the evanescence rate can be adjusted. In the case of this coating film, crystallinity can be increased to 60% by subjecting to a heat treatment at 650 degrees C. for 3 hours. However, even when the coating film is subjected to a heat treatment under higher temperature conditions, crystallinity does not increase to 90% or more.

Therefore, a coating film evanescence period can be set within a range from one week to 120 months in response to the crystallinity, composition, and thickness of the coating film formed of a calcium phosphate-based material, examples of which are shown in Table 2 below.

TABLE 2

| Evanescence Period | Composition of material | Film forming method | Film Thickness (μm) | Crystallinity (%) |
|---|---|---|---|---|
| 1 week | HA | Sputtering | 0.5 | 10 |
| 3 weeks | HA | Sputtering | 2 | 10 |
| 6 weeks | HA | Thermal Spraying | 5 | 10 |
| 3 months | HA | Thermal Spraying | 10 | 10 |
| 6 months | HA | Thermal Spraying | 20 | 10 |
| 12 months | HA | Thermal Spraying | 40 | 10 |
| 6 months | HA | Thermal Spraying | 5 | 60 |
| 12 months | HA | Thermal Spraying | 10 | 60 |
| 24 months | HA | Thermal Spraying | 20 | 60 |
| 36 months | HA | Thermal Spraying | 30 | 60 |
| 60 months | HA | Thermal Spraying | 50 | 60 |
| 120 months | HA | Thermal Spraying | 100 | 60 |

The coating film can be formed of a single layer or plural layers. Usually, since an infection rate is high immediately after an operation, it is preferred that the coating film is formed of two or more layers and an amount of an antibacterial agent or antibiotic eluted per unit time becomes larger closer to a surface layer. Since the elution amount usually depends on an evanescence rate of the coating film, the coating layer is composed of plural layers and an amount of an antibacterial agent or antibiotic eluted per unit time of each layer is adjusted by the content of the antibacterial agent or antibiotic of each layer or an evanescence rate of each layer.

The bioimplant of the present invention is used in a state of being fixed in the bone and includes artificial dental roots, artificial bone, internal fixing devices, and artificial joints. The material for the substrate of the bioimplant, for example, includes metals and alloys, such as stainless steel, cobalt-chromium alloy, titanium, and titanium alloy; ceramics such as alumina and zirconia; and plastics such as ultrahigh molecular weight polyethylene. Among these materials, metals and alloys such as cobalt-chromium alloy, titanium, and titanium alloy are preferable. The titanium alloy used includes alloys containing at least one of aluminum, tin, zirconium, molybdenum, nickel, palladium, tantalum, niobium, vanadium, and platinum added therein. A Ti-6Al-4V alloy is preferable.

The evanescent coating film of the present invention may be directly formed on a bioimplant made of a cobalt-chromium alloy or a titanium alloy. It is preferred to form the evanescent coating of the present invention on a non-evanescent calcium phosphate coating formed on an alloy implant in a conventional way.

When an artificial joint is used as the bioimplant, since the evanescent coating film of the present invention is formed so as to prevent infectious diseases, a coating position is preferably a joining portion with a joint capsule or a peripheral portion thereof.

The method of supporting an antibacterial agent or an antibiotic on the coating film of the present invention varies depending on the kind of pharmaceutical preparation. In the case of the antibiotic such as vancomycin, a method of forming a coating film first and impregnating the coating film with a dissolved antibiotic is employed. Also in the case of a liquid antibacterial agent, for example, a natural antibacterial such as hinokitiol, or an organic antibacterial agent such as benzalkonium, the same method is effective and the antibacterial agent can be used after fixing with a binder such as silane coupling. In the case of an inorganic antibacterial agent in which antibacterial activity of metal ions such as silver ion, copper ion, and zinc ion is employed, the antibacterial agent can be supported using various coating methods described above after previously supporting on a calcium phosphate-based material. Both of the antibacterial and antibiotic can be supported.

In the present invention, a metal oxide film made of at least one metal oxide having an isoelectric point of less than 7 can also be formed on at least one area of the surface of the bioimplant.

It is known that microorganisms such as bacteria have negative charge generated by dissociation of carboxyl groups or phosphoric acid groups on the surface of cells under neutral conditions. The metal oxide has an isoelectric point at which $H^+$ and $OH^-$ serve as a potential determining ion and a surface potential largely varies with the pH value of the system, and the surface potential becomes zero at a specific pH which varies depending on the kind of the metal oxide. Therefore, the metal oxide has a charge according to the isoelectric point of the aqueous solution. For example, under neutral conditions, the metal oxide having an isoelectric point of less than 7 has negative charge, whereas, the metal oxide having an isoelectric point of more than 7 has positive charge. The metal oxide used in the bioimplant of the present invention has an isoelectric point of less than 7 and therefore has negative charge under neutral conditions. Therefore, since bacteria causes electrostatic repulsion with the metal oxide used in the present invention because of the negative charge, bacteria cannot be adsorbed to the bioimplant of the present invention. As the isoelectric point decreases from 7, the negative charge density increases and electrostatic repulsion with bacteria increases, and thus bacteria are less likely to adhere. As a result, semi-permanent anti-bacterial adhesion properties can be imparted to the bioimplant of the present invention. Bacteria are adsorbed to the position serving as footing, where a biofilm is produced to cause propagation. However, since bacteria cannot be adsorbed to the bioimplant of the present invention, a biofilm cannot be produced and bacteria cannot be propagated. Thus, it becomes possible to prevent infectious diseases caused by microbial infections.

A metal oxide having an isoelectric point of less than 7 may include at least one metal oxide selected from the group consisting of silicon oxide, titanium oxide, tin oxide, niobium oxide, tantalum oxide, and chromium oxide. The isoelectric point may be a value measured by the method defined in JIS R1638 "Method or Measurement of Isoelectric Point of Fine Ceramic Powder". Silicon oxide has an isoelectric point of 1.8, rutile type titanium oxide has an isoelectric point of 6.7, anatase type titanium oxide has an isoelectric point of 6.0, tin oxide has an isoelectric point of 6.6, niobium oxide has an isoelectric point of 3.4, tantalum oxide has an isoelectric point of 2.7, and chromium oxide has an isoelectric point of 6.5. Preferred is a metal oxide having an isoelectric point of less than 6.7, for example, titanium oxide. More preferred is an anatase type titanium oxide. When two or more kinds are used, titanium oxide and silicon oxide are preferably used in combination.

The thickness of the metal oxide film can be appropriately selected within a range from 0.01 to 100 µm according to the purposes. When a thermally sprayed coating film is used, the thickness is preferably from 1 to 50 µm, and more preferably from 10 to 40 µm. When an anodized film is used, the thickness is preferably from 0.01 to 3 µm, and more preferably from 0.1 to 1.5 The metal usually has a natural oxide film and the thickness is within a range from 0.001 to 0.009 µm. Therefore, a natural oxide film has not sufficient antibacterial adhesion properties.

The metal oxide film may be composed of a single layer, or may be obtained by laminating plural layers. In the case of a multi-layered metal oxide film, only an outermost layer to be in contact with the living body can be formed of a metal oxide having an isoelectric point of 7 or less. In that case, as the material of an intermediate layer between an outermost layer and a substrate, silicon oxide, zirconium oxide, aluminum oxide, titanium oxide, magnesium oxide, zinc oxide, niobium oxide, molybdenum oxide, tantalum oxide, and hafnium oxide can be used.

With respect to a combination of the substrate and the metal oxide film of the bioimplant, it is preferred that titanium is used as the material of the substrate and titanium oxide is used as the material of the metal oxide film when the substrate is made of metal. It is preferred that alumina ceramics are used as the material of the substrate and silicon oxide is used as the material of the metal oxide film when the substrate is made of ceramics. It is preferred that an ultra-high molecular weight polyethylene is used as the material of the substrate and silicon oxide is used as the material of the metal oxide film when the substrate is made of a plastic.

In order to form a metal oxide film on a substrate made of metal or ceramics, it is possible to use known methods for forming a metal oxide, for example, thermal spraying methods such as a flame spraying method, a plasma spraying method, a high velocity oxygen fuel spraying method, an explosion spraying method, and a laser spraying method; PVD methods such as an ion mixing method, an IBAD method, and a sputtering method; and a sol-gel method. In the case of the metal substrate, oxidation treatment methods such as an atmospheric oxidation method, a chemical oxidation method, and an anodizing method can also be used. When titanium or a titanium alloy is used as the material of the substrate, the method to be used is preferably a thermal spraying method, and more preferably a flame spraying method or a high velocity oxygen fuel spraying method.

When high-temperature plasma spraying is used, a crystal structure is converted into a rutile type crystal structure. By using a low-temperature thermal spraying method such as a flame spraying method or a high velocity oxygen fuel spraying method, a large amount of an anatase type crystal having a lower isoelectric point than that of a rutile type crystal can be obtained. When a plastic is used as the material of a base material, low-temperature thermal spraying methods such as a flame spraying method and a high velocity oxygen fuel spraying method; a low-temperature PVD methods such as an IBAD method; and wet coating methods such as a sol-gel method can be used.

In order to further improve the effect of preventing infectious diseases, the metal oxide film is preferably formed at the area of a bioimplant, where an evanescent coating film is not formed, or formed as an underlying layer of an evanescent coating film. When the metal oxide film is used as the underlying layer of the evanescent coating film, adhesion of bacteria in a joint cavity can be prevented even after the evanescent coating film evanesced.

EXAMPLES

Example 1

Figure 1:
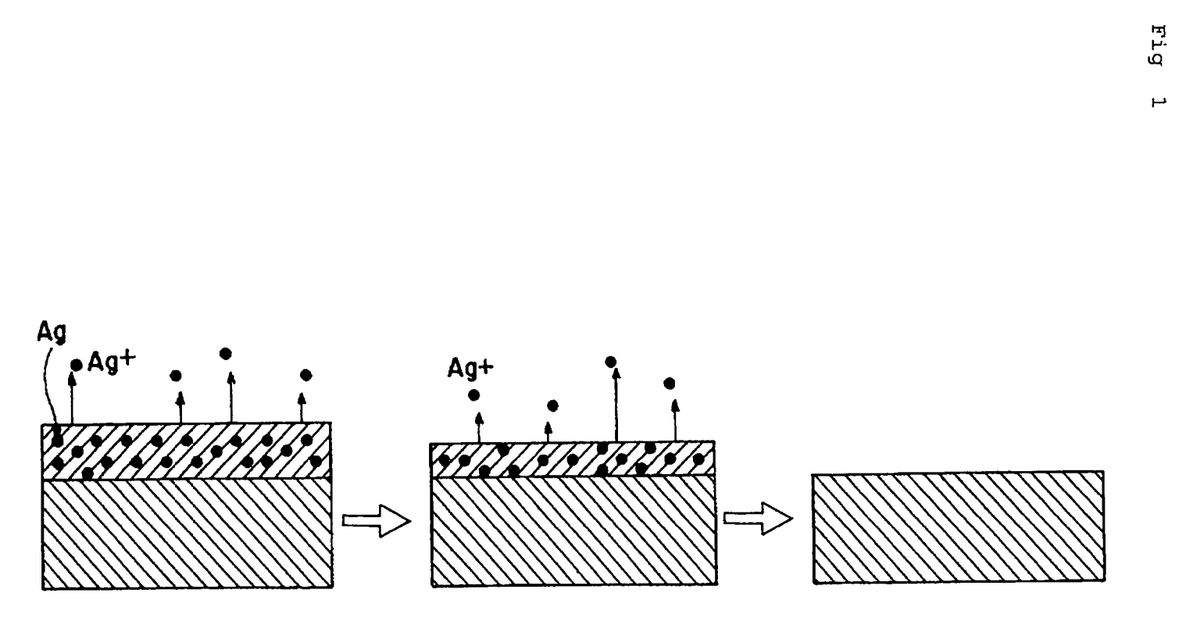
FIG. 1 is a schematic diagram showing a function of the present invention.

97% of HA and 3% of silver oxide were mixed and a thermally sprayed coating film having an average thickness of 20 μm was formed on a titanium substrate using a flame spraying method. The resulting thermally sprayed coating film had crystallinity of 10%. FIG. 1 is a schematic diagram showing a function of the present invention. The coating film formed on the titanium substrate is gradually dissolved in a body fluid and evanesced. During elution, silver ions are emitted in the body fluid.

(1) Silver Ion Elution Test

Using phosphate buffer physiological saline and bovine serum at 37 degrees C., an elution test was performed. As a result, silver ions were eluted in a concentration of 520 ppb and 4,000 ppb, respectively, after 24 hours.

(2) Antibacterial Activity Test

In accordance with JIS Z 2801, antibacterial activity against *Escherichia coli* and *Staphylococcus aureus* was evaluated. As a result, each antibacterial activity showed high values such as 4.1 and 5.0.

(3) Evanescence of Coating Film

As a result of immersion in physiological saline at 37 degrees C., a coating film was dissolved and evanesced after about 6 months.

Example 2

The coating film produced in Example 1 was subjected to a heat treatment at 650 degrees C. for 3 hours. Crystallinity was 60%. Using phosphate buffered saline and bovine serum at 37 degrees C., a silver ion elution test was performed. As a result, silver ions were eluted in a concentration of 19 ppb and 1,800 ppb, respectively, after 24 hours. Elution characteristics drastically varied by changing crystallinity.

Example 3

97% of HA and 3% of silver oxide were mixed and a coating film having an average thickness of 2 μm was formed on a titanium substrate using a sputtering method. The resulting coating film had crystallinity of 10%.

(1) Silver Ion Elution Test

An elution test was performed in bovine serum at 37 degrees C. As a result, silver ions were eluted in a concentration of 280 ppb after 24 hours.

(2) Antibacterial Activity Test

In accordance with JIS Z 2801, antibacterial activity against *Escherichia coli* and *Staphylococcus aureus* was evaluated. As a result, each antibacterial activity showed effective values such as 2.4 and 2.8.

(Note)

In accordance with JIS Z 2801, the case where antibacterial activity shows a value of 2.0 or more is rated that the coating film has antibacterial activity.

(3) Evanescence of Coating Film

As a result of immersion in physiological saline at 37 degrees C., a coating film was dissolved and evanesced after about 3 weeks.

Example 4

3% of silver oxide and 97% of .alpha.-TCP were mixed and a coating film having an average thickness of 40 μm was formed on a titanium substrate using a flame thermal spraying method. The resulting coating film had crystallinity of 100%.

(1) Silver Ion Elution Test

An elution test was performed in bovine serum at 37 degrees C. As a result, silver ions were eluted in a concentration of 12,000 ppb after 24 hours.

(2) Antibacterial Activity Test

In accordance with JIS Z 2801, antibacterial activity against *Escherichia coli* and *Staphylococcus aureus* was evaluated. As a result, each antibacterial activity showed high values such as 6.4 and 6.2.

Example 5

Using a calcium phosphate-based glass powder containing 1.85% of silver, a thermally sprayed coating film having an average thickness of 40 μm was formed on a titanium substrate by a flame spraying method. The resulting coating film was amorphous.

(1) Silver Ion Elution Test

An elution test was performed in bovine serum at 37 degrees C. As a result, silver ions were eluted in a concentration of 2,500 ppb after 24 hours.

(2) Antibacterial Activity Test

In accordance with HS Z 2801, antibacterial activity against *Escherichia coli* and *Staphylococcus aureus* was evaluated. As a result, each antibacterial activity showed high values such as 7.8 and 4.9.

Example 6

Application to Artificial Hip Joint

Figure 2A:
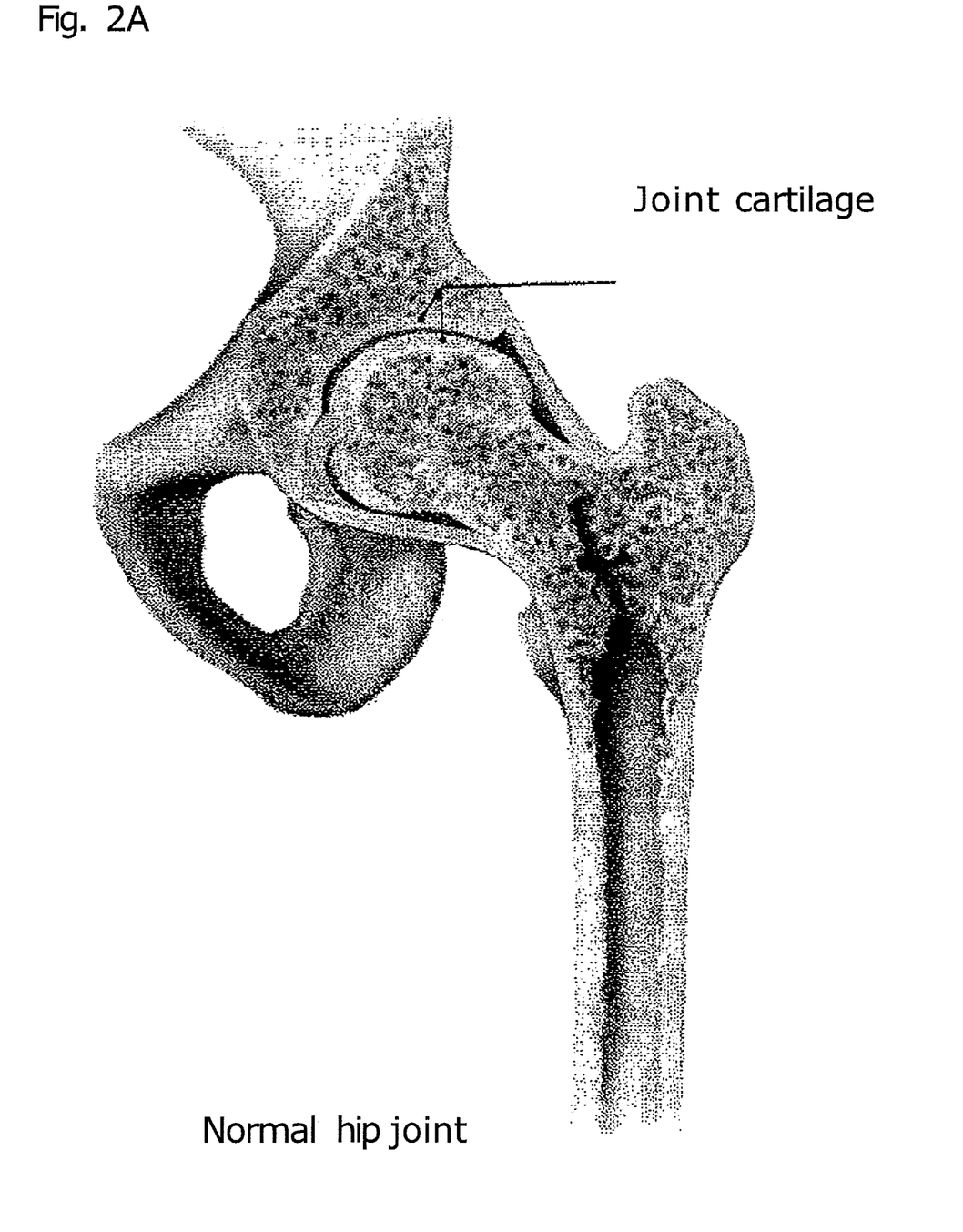
FIG. 2A is a sectional view showing a normal hip joint.
Figure 2B:
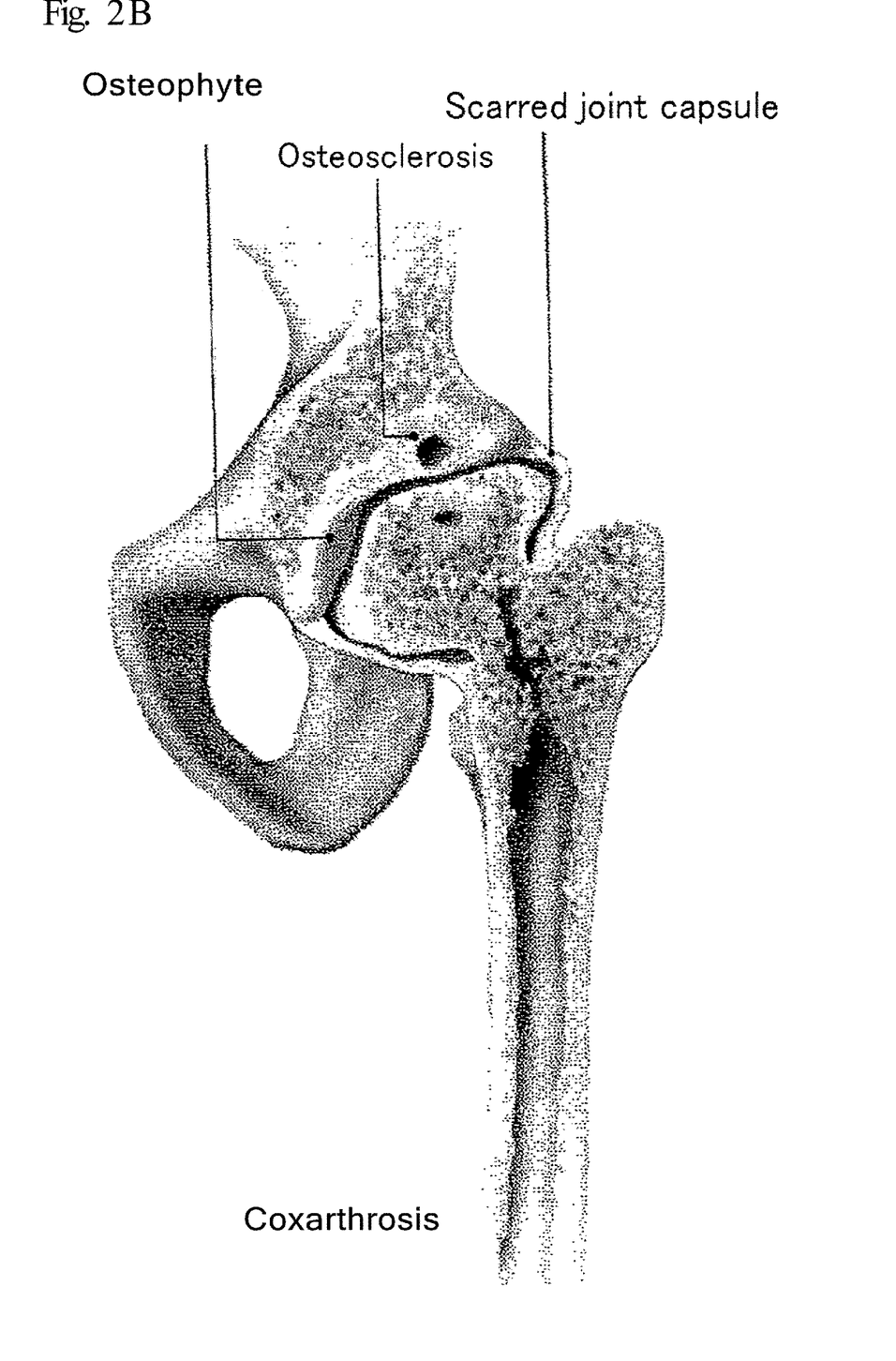
FIG. 2B is a sectional view showing a hip joint suffering from osteoarthritis.
Figure 2C:
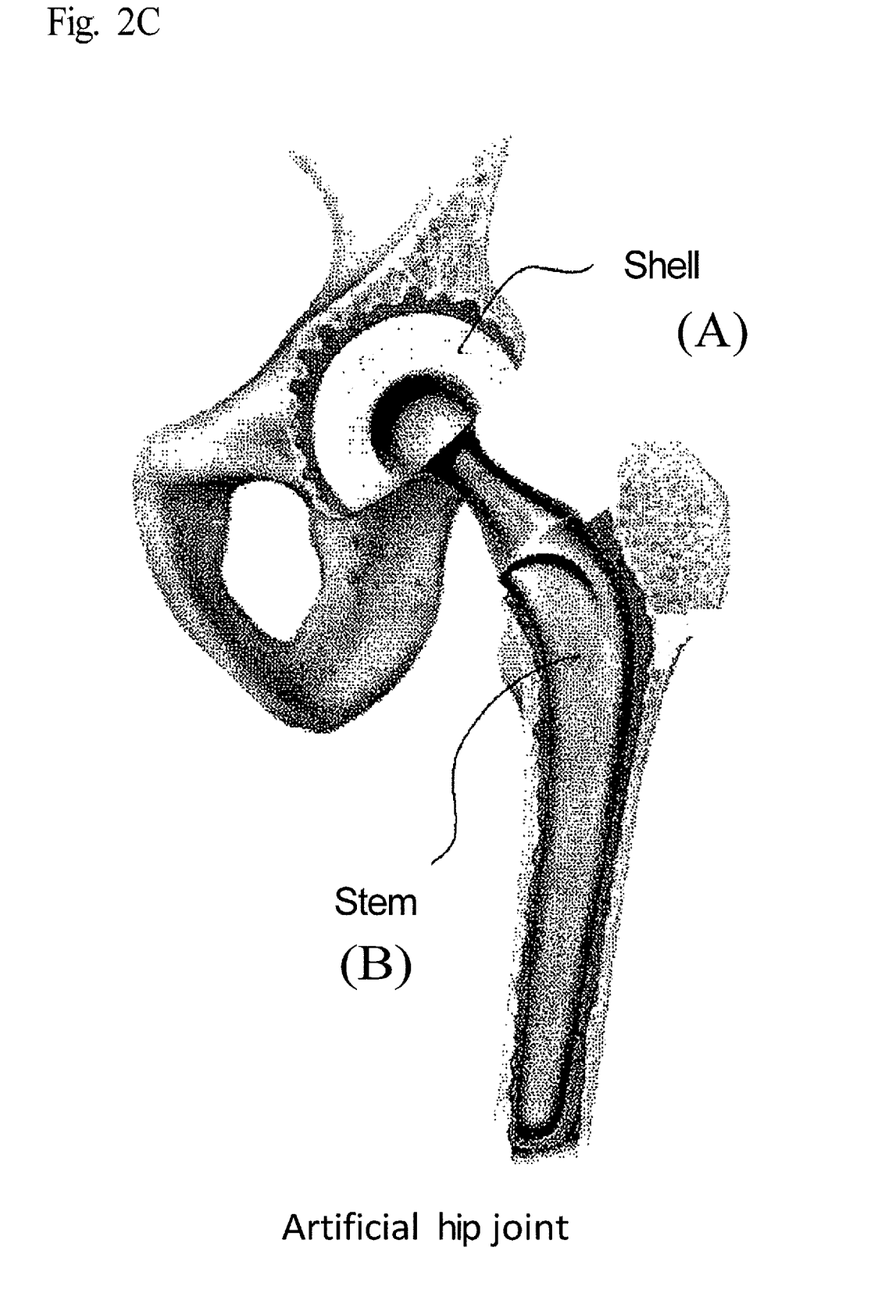
FIG. 2C is a sectional view showing a joint portion of a hip joint to which an artificial hip joint has been applied.
Figure 3:
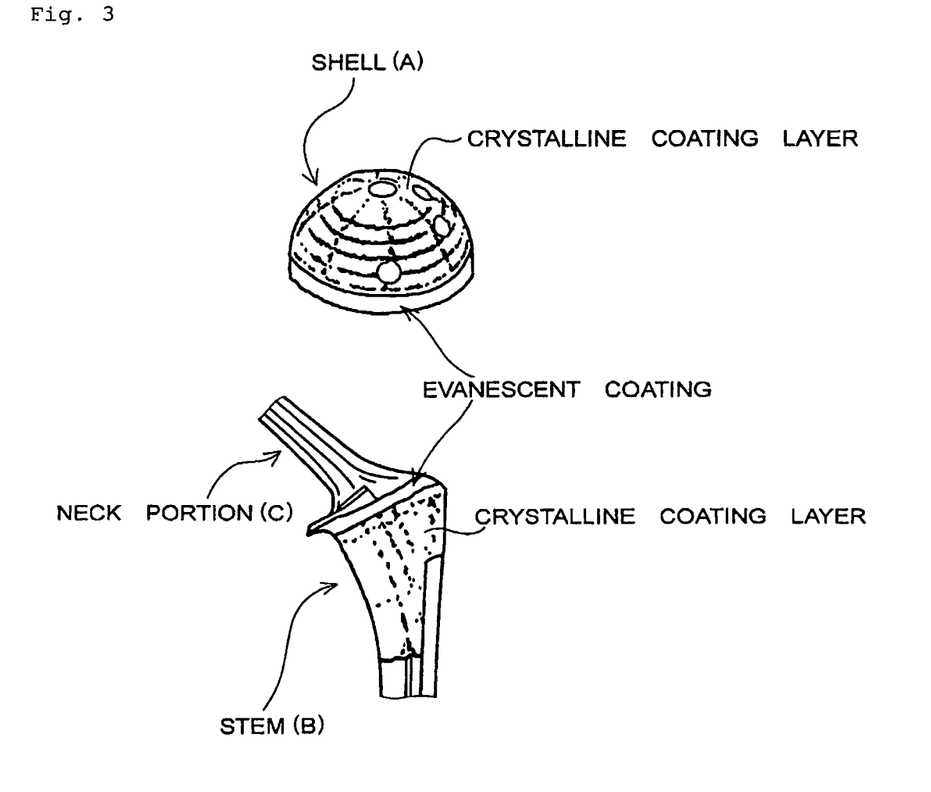
FIG. 3 is a perspective view showing a shell (A) and a stem (B) of an artificial hip joint.

FIG. 2A is a sectional view showing a normal hip joint, FIG. 2B is a sectional view showing a hip joint suffering from osteoarthritis, and FIG. 2C is a sectional view showing a joint portion of a hip joint to which an artificial hip joint has been applied. FIG. 3 is a perspective view showing a shell (A) and a stem (B) of an artificial hip joint (source: Illustrated Lecture of Orthopedic Diagnostic Treatment (Zusetsu Seikeigeka Shindan Chiryo Koza), Vol. 15, "Artificial Joint/Biomaterial", Kagehisa Murode). In FIG. 2B, production of osteophyte, osteosclerosis and scarred joint capsule is recognized as a result of change of joint cartilage.

A shell (A) is made of a Ti alloy and a crystalline HA coating film is formed over the entire surface of an upper hemispherical portion, while an evanescent coating film is formed at the lower peripheral portion of the coating film of the shell (A) in the same manner as in Example 1. In contrast, a crystalline HA coating film is formed under a neck of a stem (B), while an evanescent coating film is formed at the upper peripheral portion of the coating film in the same manner as in Example 1.

Since the evanescent coating film is formed at the portion around a joint capsule, which enables bacterial access, it is possible to prevent bacterial infection from the joint capsule. Therefore, the onset of infectious diseases after the implantation operation can be prevented.

Example 7

An anatase type titanium oxide (particle size: 5 μm) was accumulated on a titanium substrate by a high-velocity oxygen fuel spraying method to form a metal oxide film having an average thickness of about 20 μm.

A specimen measuring 50.times.50.times.2 mm comprising a titanium oxide layer formed on the surface was placed on a polystyrene plate and, after immersing in Tryptic Soy Broth (TSB)+glucose liquid culture medium, 150.mu.1 of a solution of strains of precultured "Methicillin-Resistant Staphylococcus Aureus (MRSA clinically isolated strains) having biofilm-forming ability" was inoculated. After static culture in an incubator at 37 degrees C. under sunlight-shielding conditions for 120 hours, the specimen was washed twice with distilled water and then stained with crystal violet. When bacteria are propagated and a biofilm is formed on the surface, the stained portion is stained red. A specimen having no titanium oxide layer formed on the surface was used as a control and a test was performed in the same manner.

The entire surface of the control specimen was stained red, whereas, the specimen having a titanium oxide layer formed on the surface contains a small stained portion, which shows inhibition of propagation of bacteria. As a result of palpation, the surface of the control specimen showed a slimy feel and the presence of a thick bioflim layer was confirmed. In contrast, the surface of the specimen having a titanium oxide layer formed on the surface did not show the slimy feel.

Example 8

A titanium substrate was washed in hydrofluoric acid and then anodized in an aqueous phosphoric acid solution to form an anatase type titanium oxide film having a thickness of about 0.14 μm on the surface.

The surface of the control specimen was stained red similar to Example 1, whereas, the surface of the specimen having a titanium oxide layer formed on the surface was strained slightly light red, which shows inhibition of propagation of bacteria. The results of palpation were the same as those in Example 1.

Example 9

A crystalline silicon oxide (particle size: 35 μm) was accumulated on a titanium substrate by a flame spraying method to form a metal oxide film having an average thickness of about 20 μm.

The entire surface of the control specimen was stained red similar to Examples 1 and 2 whereas, the stained portion scarcely existed at only some area in the specimen having a titanium oxide layer formed on the surface was strained slightly light red, which shows inhibition of propagation of bacteria. The results of palpation were the same as those in Examples 1 and 2.

Example 10

An anatase type titanium oxide (particle size: 5 μm) was accumulated on a titanium substrate by a high velocity oxygen fuel spraying method to foam a metal oxide film having an average thickness of about 20 μM.

A specimen measuring .phi.14.times.1 mm comprising a titanium oxide film formed on the surface was placed on a polystyrene plate and immersed in 500.mu.1 of a 1/500 natural broth in which an amount of bacteria is adjusted by adding a predetermined amount of precultured "Methicillin-Resistant Staphylococcus Aureus (MRSA clinically isolated strains) having a biofilm-forming ability", followed by culture in an incubator at 37 degrees C. for 6 hours. The surface of the specimen was rinsed twice with 500.mu.1 of PBS(−) and, after adding 10 ml of PBS(−), ultrasonic cleaning was performed for 5 minutes. The wash was collected and the number of adhered living bacteria was measured. An initial amount of inoculated bacteria was 2.2.times.10.sup.6 CFU/well. As a control of this bacterial culturing test, a pure titanium disk having the same shape was used. Five specimens were used in the test. The titanium disk used as the control has a natural oxide film.

The number of living bacteria was 64.8 CFU on average in the specimen having a titanium oxide film formed on the surface, whereas, the number of living bacteria was 19481 CFU on average in the control specimen. In the specimen having a titanium oxide film formed on the surface, it could be confirmed that adhesion of bacteria is significantly inhibited and the specimen has sufficient bacteria adhesion inhibitory ability.

Example 11

A crystalline silicon oxide (particle size: 35 μm) was accumulated on a titanium substrate by a flame spraying method to form a metal oxide film having a thickness of about 20 μm.

The number of adhered bacteria was measured in the same manner as in Example 10. In the specimen having a titanium oxide film formed on the surface, the number of adhered bacteria was less than about 10 CFU. In the specimen having a crystalline silicon oxide film formed on the surface, it could be confirmed that adhesion of bacteria is significantly inhibited and the specimen has sufficient bacteria adhesion inhibitory ability.

Example 12

Application to Artificial Hip Joint

Figure 4:
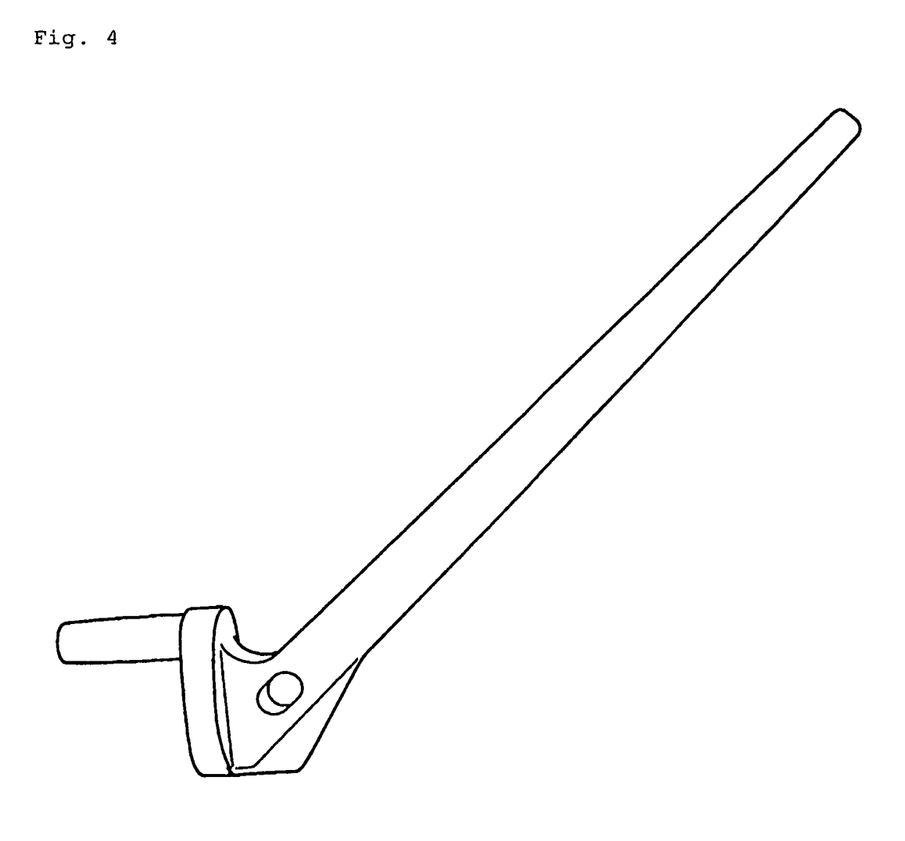
FIG. 4 is a photograph showing the appearance of a stem produced experimentally in Example 12.

By a high velocity oxygen fuel spraying method, an anatase type titanium oxide (particle size: 5 μm) was coated on the neck portion of a stem of an artificial hip joint of Example 6 to form a metal oxide film. The stem was coated with hydroxyapatite containing 3% of silver oxide added therein in a range from the collar to the position located about 5 mm under the collar by a flame spraying method to form an evanescent coating film. Furthermore, the stem was coated with hydroxyapatite in a range from the position located 5 mm under the collar to the bottom end of the stem by a flame spraying to form a crystalline coating film. Any film thus formed had a thickness of 20 μm. FIG. 4 is a photograph showing a stem produced experimentally.

The negative charge of metal oxide makes it impossible for bacteria to adhere to the neck portion. The evanescent coating film exerts, in addition to the effect of preventing bacterial access through a joint capsule, an effect of preventing adhesion of bacteria in a joint cavity.

A metal oxide film can be formed at a neck portion, and also formed in a range where a crystalline coating film of a stem (B) is not formed. When the metal oxide film is used as an underlying layer of the evanescent coating film, it is possible to prevent adhesion of bacteria in a joint cavity even after evanescence of the evanescent coating film.

Example 13

Referring to Table 3 below, four specimens A to D were prepared. All of the specimens A to D included thermally sprayed coating films formed on a titanium substrate by a flame spraying method. The titanium substrate has a diameter of 40 mm and a thickness of 2 mm. Average thicknesses of a coating film on the titanium substrate of the specimens were 40 μm. The thermally sprayed material was formed from a mixture of 97% HA and 3% silver oxide for Specimens A and B, and 100% of HA which does not include silver oxide for Specimens C and D. Specimens B and D were processed by heating treatment with 650° C. under reduced pressure atmosphere after the thermal spraying process, whereas Specimens A and C were not. The crystallinity measured by common X-ray diffraction method was 10% for Specimens A and C and 60% for Specimens B and D.

Immersion Experiment

All of the Specimens A to D were immersed into 100 ml of normal saline. After the predetermined time from the immersion, 2 ml of the normal saline was collected and measured by Inductively Coupled Plasma (ICP) optical emission spectrometry for the quantitative analysis of Ca concentration. The predetermined times were set to 1 hour, 3 hours, 6 hours, and 24 hours respectively. The measurement result is shown in the table below.

TABLE 3

| Specimen | Ratio of silver oxide (%) | Crystallinity (%) | Ca concentration (ppm) by each immersing time (Hr) | | | | |
|---|---|---|---|---|---|---|---|
| | | | 0 Hr | 1 Hr | 3 Hrs | 6 Hrs | 24 Hrs |
| A | 3 | 10 | 0 | 2.09 | 4.19 | 6.27 | 11.8 |
| B | 3 | 60 | 0 | 0.91 | 1.3 | 1.76 | 2.81 |
| C | 0 | 10 | 0 | 2.18 | 3.88 | 5.8 | 10.9 |
| D | 0 | 60 | 0 | 0.99 | 1.3 | 1.54 | 2.68 |

Ca concentration for all of the Specimens A to D increased with time. It is estimated that the increase of Ca concentration indicates the dissolution of calcium phosphate of the thermally sprayed coating film, and the increase of Ca concentration is proportionate to the speed of evanescence of the thermally sprayed coating film. Specimens A and C having 10% crystallinity included approximately four times higher Ca concentration as Specimens B and D having 60% crystallinity after 24 hours of the immersion. Thus, it is estimated that the evanescence speed of the thermally sprayed coating film is approximately four times faster for coatings having 10% crystallinity compared to similar coating thicknesses having 60% crystallinity. In other words, the evanescence period of the thermally sprayed coating film having 60% of crystallinity should be approximately four times longer than the evanescence period of the thermally sprayed coating film having 10% of crystallinity and the same thickness, as shown in Table 2 above.

In example 1, the thermally sprayed coating film having a thickness of 20 μm and 10% of crystallinity evanesced in 6 months under the long-term immersion experiment. Therefore, it is estimated that the evanescence periods of the thermally sprayed coating film having 10% of crystallinity are 1.5 months for the thermally sprayed coating film having 5 μm. And therefore, it is estimated that the evanescence periods of the thermally sprayed coating film having 60% of crystallinity are 6 months for the thermally sprayed coating film having 5 μm, 12 months for the thermally sprayed coating film having 10 μm, 24 months for the thermally sprayed coating film having 20 μm, 36 months for the thermally sprayed coating film having 30 μm, 60 months for the thermally sprayed coating film having 50 μm, and 120 months for the thermally sprayed coating film having 100 μm. The antibacterial property provided by silver included in the coating film should last until the thermally sprayed coating film completely evanesces. Thus, the duration of antibacterial properties of an implant having a coating film in accordance with various embodiments of the invention can be controlled in accordance with particular needs and/or applications.

In some embodiments, the present invention is applied to bioimplants such as artificial bone, internal fixing device and artificial joint and can adjust crystallinity of an evanescent coating film, adjust release rate of an antibacterial agent and an antibiotic by the composition, and adjust a release period by thickness of the film, and is therefore most suited for prevention of infectious diseases of a bioimplant. Since evanescence of the coating film can be utilized, there is an advantage that an inorganic antibacterial agent can be effectively utilized. Furthermore, formation of a metal oxide film made of one or more metal oxides having an isoelectric point of less than makes it possible to impart semi-permanent anti-bacterial adhesion properties to the bioimplant, thus making it possible to further improve the effect of preventing infectious diseases.

What is claimed is:

1. A bioimplant comprising:
   an implant comprising a metal or metal alloy material; and
   an evanescent coating film comprising a calcium phosphate-based material having crystallinity of 10% to 90%, the evanescent coating film containing an inorganic antibacterial agent,
   wherein the inorganic antibacterial agent comprises silver metal or silver oxide,
   wherein the evanescent coating film is free of any oxide of the metal or metal alloy material except the calcium phosphate-based material and the inorganic antibacterial agent, and
   wherein a thickness of the evanescent coating film is between 5 and 100 micrometers (μm).

2. The bioimplant according to claim 1, wherein the inorganic antibacterial agent comprises silver metal particles distributed in the evanescent coating film.

3. The bioimplant according to claim 1, wherein the calcium phosphate-based material comprising at least one material selected from the group consisting of: hydroxyapatite (HA), tertiary calcium phosphate (TCP) and quaternary calcium phosphate (TeCP).

4. The bioimplant according to claim 1, wherein the thickness of the evanescent coating film is between 20 and 100 micrometers (μm).

5. The bioimplant according to claim 1, wherein an elution period of the inorganic antibacterial agent when the implant is placed in a body fluid is at least six months.

6. The bioimplant according to claim 1, wherein the implant comprises a metal or metal alloy material.

7. The bioimplant according to claim 1, wherein the evanescent coating film is formed on the implant by a thermal spraying method.

8. The bioimplant according to claim 7, wherein the thermal spraying method is selected from a group consisting of a flame spraying, a high velocity oxygen fuel spraying, and a plasma spraying method.

9. A bioimplant for an artificial joint comprising:
an implant; and
an evanescent coating film formed on a surface of the implant by a thermal spraying method, wherein the evanescent coating film comprises:
a calcium phosphate-based material having a crystallinity of 10% to 90%
and
an inorganic antibacterial agent comprising a silver metal, silver oxide, or a combination thereof, wherein a thickness of the evanescent coating film is between 5 and 100 micrometers (μm) and wherein an evanescence period of the evanescent coating film is at least six weeks when the implant is placed in a body fluid.

10. The bioimplant according to claim 9, wherein the evanescent coating film is directly formed on the implant or on a non-evanescent calcium phosphate coating formed on the implant.

11. The bioimplant according to claim 9, wherein the calcium phosphate-based material comprises at least one material selected from the group consisting of hydroxyapatite (HA), tertiary calcium phosphate (TCP) and quaternary calcium phosphate (TeCP).

12. The bioimplant according to claim 9, wherein the implant comprises a metal or metal alloy material and the evanescent coating film is free of any oxide of the metal or metal alloy material.

13. The bioimplant according to claim 9, wherein the thermal spraying method is selected from the group consisting of a flame spraying, high velocity oxygen fuel spraying, and plasma spraying method.

14. A bioimplant, comprising:
an implant comprising a metal or metal alloy material; and an evanescent coating film formed on the implant by thermal spraying, wherein the evanescent coating film comprises a calcium phosphate-based material having a crystallinity of 10% to 90%, said calcium phosphate-based material being mixed with an inorganic antibacterial agent such that inorganic antibacterial agent particles are distributed in the coating, wherein the evanescent coating film is free of any oxide of the metal or metal alloy material and is directly formed on a surface of the implant or on a non-evanescent calcium phosphate coating formed on the implant surface, and
wherein a thickness of the evanescent coating film is between 5 and 100 micrometers (pm) and an evanescence period of the evanescent coating film is at least six weeks when the implant is placed in a body fluid.

15. The implant of claim 14, wherein the inorganic antibacterial agent particles comprise silver metal particles.

16. The implant of claim 14, wherein the inorganic antibacterial agent particles comprise silver oxide particles.

17. The implant of claim 14, wherein the evanescent coating film has an evanescence period of at least three months when the implant is placed in a body fluid.

18. The implant of claim 14, wherein the calcium-phosphate-based material comprises hydroxyapatite, β-tertiary calcium phosphate, or a mixture of both.

19. The implant of claim 14, wherein a thickness of the evanescent coating film is 20 pm to less than 40 μm.

20. The implant of claim 14, wherein a thickness of the evanescent coating film is 40 μm to less than 100 μm.

* * * * *